(12) United States Patent
Torres

(10) Patent No.: US 7,025,283 B2
(45) Date of Patent: Apr. 11, 2006

(54) AIR FRESHENER FOR MOTOR VEHICLES

(75) Inventor: David Fernandez Torres, Almeria (ES)

(73) Assignee: L & D, S.A., Huercal de Almeria (ES)

(*) Notice: Subject to any disclaimer, the term of this patent is extended or adjusted under 35 U.S.C. 154(b) by 122 days.

(21) Appl. No.: 10/659,697

(22) Filed: Sep. 11, 2003

(65) Prior Publication Data

US 2004/0129742 A1  Jul. 8, 2004

(30) Foreign Application Priority Data

Sep. 11, 2002  (ES)  ............................ 200202204 U

(51) Int. Cl.
   *A24F 25/00*  (2006.01)
   *A61L 9/04*  (2006.01)
(52) U.S. Cl. ..................... 239/34; 239/42; 239/43; 239/44; 239/51.5; 239/53
(58) Field of Classification Search ............... 239/34, 239/42, 43, 44, 51.5, 53, 55–57
   See application file for complete search history.

(56) References Cited

U.S. PATENT DOCUMENTS

| 5,422,078 | A | * | 6/1995 | Colon | ................. 422/123 |
| 5,478,505 | A | * | 12/1995 | McElfresh et al. | ............ 261/30 |
| 5,865,372 | A | * | 2/1999 | Ceresko | ................. 239/60 |
| 5,899,382 | A | * | 5/1999 | Hayes et al. | ................. 239/56 |
| 6,102,660 | A | * | 8/2000 | Lee | ................. 416/146 R |

* cited by examiner

*Primary Examiner*—Davis Hwu
(74) *Attorney, Agent, or Firm*—Jacobson Holman PLLC

(57) ABSTRACT

An air freshener is composed of a diffuser with a wick system that is impregnated with a liquid fragrance contained in a replaceable bottle or receptacle whose liquid perfume, which is made and included in concentrate form, is obtained from natural essences to provide a long life. The air fresher is provided with an adjustment for the volume of the air freshener by volatilization of the fragrant product by a simple turn of the head cap, at the user's discretion. It is possible to stop the product from issuing when the vehicle is not in use, thus saving its consumption.

3 Claims, 2 Drawing Sheets

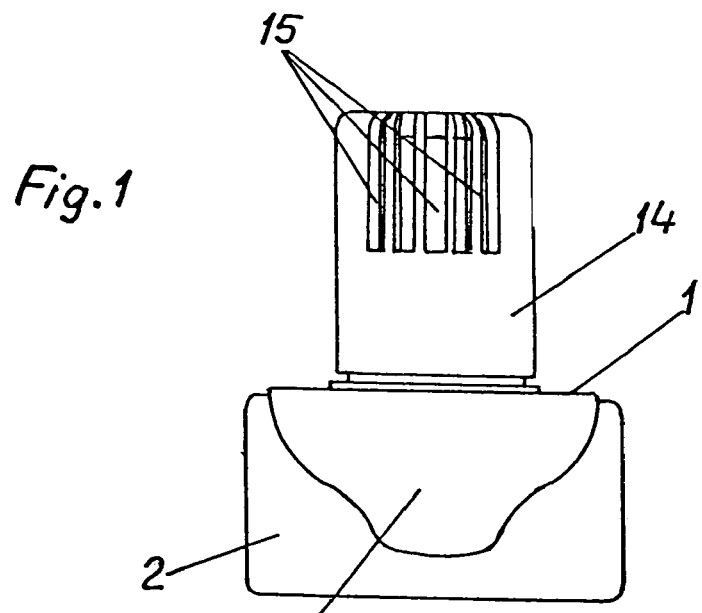
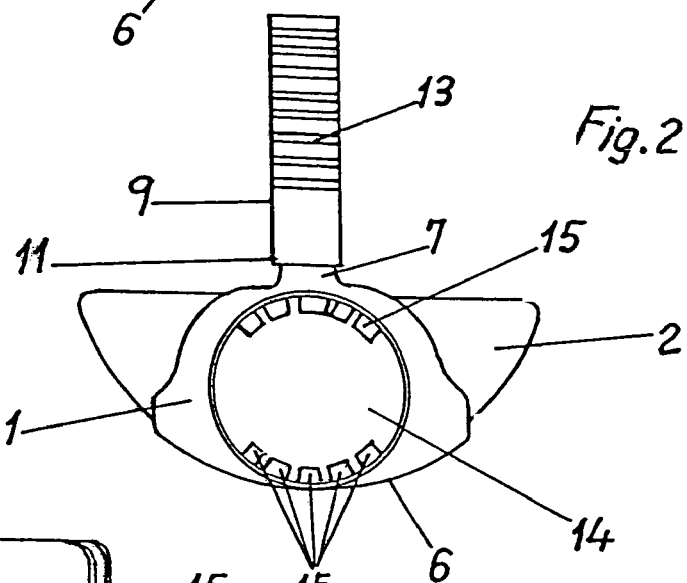
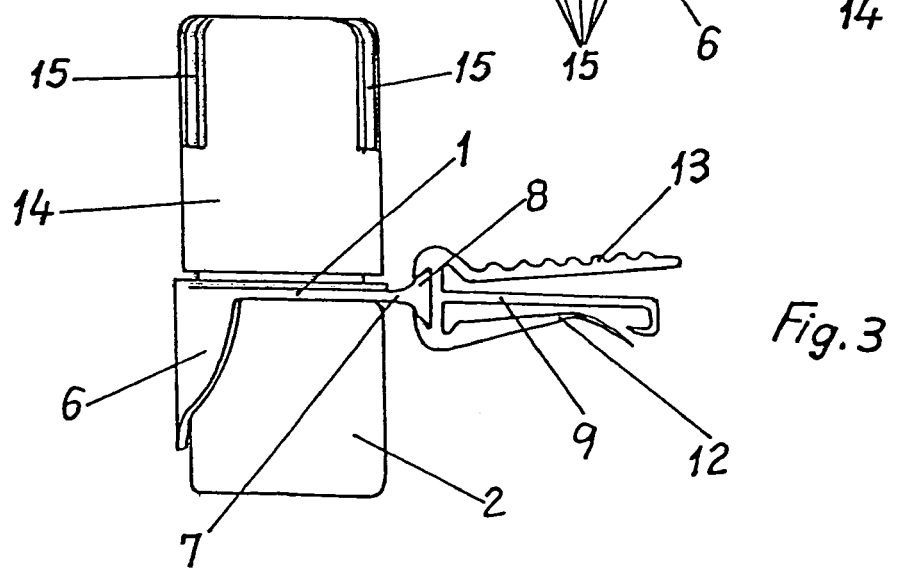

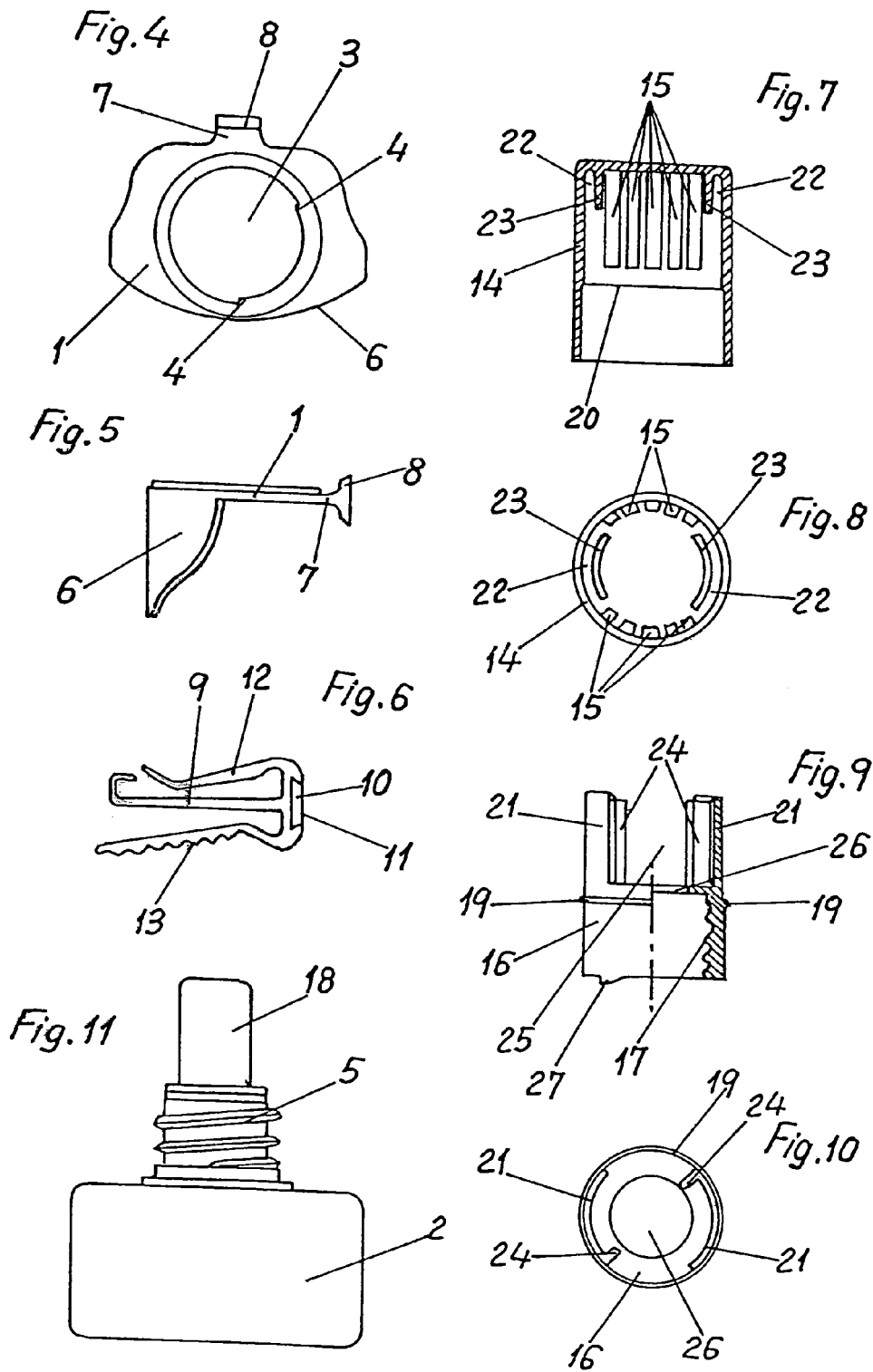

AIR FRESHENER FOR MOTOR VEHICLES

FIELD OF THE INVENTION

The present invention relates to a new air freshener for motor vehicles with improvements that represent an innovation in the field of air fresheners.

SUMMARY OF THE INVENTION

The air freshener of the present invention is composed of a diffuser with a wick system that is impregnated with a liquid fragrance contained in a replaceable bottle or receptacle whose liquid perfume, which is made and included in concentrate form, is obtained from natural essences to provide a long life. The air fresher is provided with means to adjust the volume of the air freshener by volatilisation of the fragrant product by means of a simple turn of the head cap, at the user's discretion. It is possible to stop the product from issuing when the vehicle is not in use, thus saving its consumption. Using for this purpose an original design with an exclusive adjustable cap system, resulting in a highly attractive and efficient air freshener of simple use, presenting structural and constitutive features that differ noticeably from the currently known means for these purposes.

The improved air freshener for motor vehicles of the present invention is made up of a support which comprises in its lower part the removable and replaceable bottle or receptacle containing the liquid fragrant product, while in the top part the bottle and support include a rotary cap, provided with radial slots through which the fragrant product issues and is diffused by means of its evaporation. The cap is able to open up or shut off the issue of the air freshener product at the user's discretion.

At the back of the freshener bottle holder and diffuser cap there is a projecting central dovetailed appendix acting as a support on which a kind of clip is fitted by sliding it into place, up to a stop, which secures the air freshener to the dashboard of the car by being pressed between the air conditioning grilles or at any other suitable place of easy access for the user.

These and other objects of the invention, as well as many of the intended advantages thereof, will become more readily apparent when reference is made to the following description taken in conjunction with the accompanying drawings.

BRIEF DESCRIPTION OF THE DRAWINGS

For clearer understanding of the general features described above drawings are attached that illustrate in a graphic and diagrammatic form a case of practical embodiment of the improved air freshener for motor vehicles, making it quite clear that, in view of the primarily informative nature of the drawings in question, the figures designed in them should be examined in the broadest sense without imposing any limitation.

The figures represented in the adjoining drawings show views as specified below:

FIG. 1 is a front elevational view of the air freshener of the present invention, showing the lower bottle or receptacle containing the fragrant product, fitted on an intermediate support with projection at the back, the rotary freshener product dispensing cap, provided with grilles at two diametrically opposed points, through which the output volume of freshener product may be dispensed by hand.

FIG. 2 is a plan view of the air freshener of the present invention, showing the arrangement of the freshener grilles machined at two opposing points of the rotary cap, and at the center of the back of the air freshener there is also a dovetailed projection where a kind of clip is fitted that enables the air freshener to be attached to the dashboard of the motor vehicle between the air conditioning grilles or elsewhere.

FIG. 3 is a side elevational view of the air freshener of the present invention according to FIGS. 1 and 2, where it is observed not only the system of installation of the freshener product container bottle from underneath the central support, which is secured by screwing the upper rotary cap, which in turn is used to seal or open up the freshener product outlet grille with a simple turn, but also the centered arrangement of the dovetail projection at the middle of the back of the central support for fitting a clip with adjustable attachment to the vehicle dashboard.

FIG. 4 is a plan view of the piece that forms the general support of the air freshener with the rear hook for the attachment support clip, showing a step that prevents the movement of the bottle and the upper cap in the freshener product container bottle central fitting hole.

FIG. 5 is an elevational profile view of the intermediate installation part where the dovetailed attachment projection and the front plate are seen.

FIG. 6 is a profile view of the clip for attaching the air freshener to the vehicle dashboard pressed between the air conditioning grilles.

FIG. 7 is a diametral section of the rotary cap the inside of which is provided, next to the top finish, with descending arched pieces that guide the turning of the actual cap for freshening purposes, showing between said arched projections the grilles for adjusting the outlet for freshening purposes, as well as the internal step for housing the inner bushing that screws onto the container bottle, provided in its upper section with outlet grilles.

FIG. 8 is an interior view from the base of the rotary cap, showing at the bottom the arched projections that guide the turning of the actual cap in its functions of either shutting off or opening up the air freshener outlet.

FIG. 9 is an elevational view with half section of the internal bushing for housing in the rotary cap, with the lower inside threading for attachment to the freshener product container bottle, with two arched projections at the top at two diametrically opposed points, as a means for sealing the grilles through which the air freshener product is diffused, being provided with travel end stops that limit how far the sealing cap can turn.

FIG. 10 is an upper plan view of the cap internal bushing from the arched projections adjacent to the outlet grilles machined in the cap, one of the ends of said arched pieces having a radial projection that acts as a turn limiting stop.

FIG. 11 is an elevational front view of the freshener product container bottle provided with a wick sealed with a tubular piece, which is removable at the time of use.

DETAILED DESCRIPTION OF THE PREFERRED EMBODIMENTS

With reference to the adjoining drawings, it has to be mentioned that the different figures contain reference numbers relating to the descriptions of their characteristics and operation as set out below, thereby assisting their prompt identification, 1 being the central piece to which the bottle or receptacle 2 is fitted by way of the through-hole 3 provided with an internal step 4 to prevent the upper threaded part 5 of the bottle 2 from being able to turn or move.

At the front, the central support piece 1 has a bearing plate 6 on the front of the bottle 2, while, centrally located on the back, the aforesaid piece 1 is provided with a projection 7 ending in a male dovetail 8, where the clip part 9 is fitted by way of the female dovetail recess 10 provided with a wall 11 that limits its insertion.

The clip part 9 has upper and lower flexible or spring action pieces 12 and 13 provided with stepping, respectively, by means of which the air freshener can be attached to the vehicle dashboard, to the air-conditioning outlet grilles or anywhere else as my be required.

The air freshener product contained in the bottle or receptacle 2 is dispensed by means of the rotary cap 14 which is provided with outlet grilles 15 machined at the top at two diametrically opposed points, said rotary cap 14 being fitted with an inner bushing 16 which has a threaded sector on the inside at the bottom for attaching the bottle or receptacle 2 by means of its upper threaded portion 5 after first removing the tubular body 18 and exposing the internal wick impregnated with freshener liquid.

The bushing 16 housed in the rotary cap 14 is inserted until the peripheral ridge 19 of the actual bushing 16 goes beyond the step 20 in the cap 14, with the result that the ascending arched projections 21 at the top of the bushing 16 are engaged in the channels 22 obtained by the descending guides 23 that form an integral part of the rotary cap 14 in hanging form from its head, said ascending projections 21 from the inner bushing 16 acting as seals for the grilles 15 on both sides of the cap 14 either to shut off or to allow the freshener product to issue, for which purpose the upper projections 21 of the bushing 16 each have radial projections 24 at one end, which act as stops in the open and closed positions, thereby limiting the rotary movement of the cap 14 in its freshening function, so that the wick is impregnated with the liquid freshener product in the space 25 in the hole 26 passing through the center of the bushing.

Finally, it should be mentioned that at a point on the bottom edge of the bushing 16 there is a protruding tab 27 that acts as a detent, not involved in the turning movements of the cap 14, except only if forced when greater pressure is exerted at the time of proceeding to exchange or replace the bottle or receptacle 2 containing the liquid freshener product.

Considering that each and every one of the parts making up the improved air freshener for motor vehicles in question have been amply describe, it only remains to point out that its different components may be made in a variety of materials, sizes, shapes and colors, while those modifications of a structural nature advocated by practice may also be introduced, providing that they do not alter the essential points of the invention which is the object of the present invention.

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar purpose.

The foregoing description should be considered as illustrative only of the principles of the invention. Since numerous modifications and changes will readily occur to those skilled in the art, it is not desired to limit the invention to the exact construction and operation shown and described, and, accordingly, all suitable modifications and equivalents may be resorted to, falling within the scope of the invention.

I claim:

1. An air freshener for a motor vehicle comprising
   an intermediate support piece including a horizontal planar surface having a hole in a middle,
   a liquid freshener product container bottle or receptacle fitted from underneath by insertion through the hole of the intermediate support piece,
   a freshener product rotary dispensing cap fitted on an upper threaded end of the freshener product container bottle, the freshener product rotary dispensing cap being applied on the intermediate support, the intermediate support having a descending plate on a front plane attachable to the liquid freshener product container bottle, the intermediate support piece having, on a rear side, a horizontal projection with a male dovetailed anchorage system for attachment to the motor vehicle, and
   a clip provided with a female dovetailed anchorage with a lateral insertion stop fitted in said male dovetailed anchorage system, said clip having flexible projecting arms for press-fitting between air-conditioning grilles of the motor vehicle or at any other point on a dashboard.

2. The air freshener for a motor vehicle, according to claim 1, wherein the freshener product rotary dispensing cap has dispensing grilles, in an upper half, at two diametrically opposing points, while an inside of said cap has a tight-fitting bushing, a lower inner portion of the bushing comprises a threaded sector which attaches the freshener product rotary dispensing cap at an upper projecting threading of the freshener bottle, said bushing is provided at a point half-way up with a projecting ridge for coupling the bushing on the inside of the freshener product rotary dispensing cap with a machined step of the freshener product rotary dispensing cap, and the bushing has, above the step, ascending arched projections at two diametrically opposed points, the arched projections engage, at an upper end, in channels in an upper inside portion of the freshener product rotary dispensing cap, the ascending arched projections of the bushing are for opening up or sealing off the dispensing grilles in the freshener product rotary dispensing cap, the freshener product rotary dispensing cap is provided with a fully-open and fully-closed stops, the stops consisting of radial pieces integral with the bushing, and the stops perform travel limiting action on descending arched pieces in the upper inside portion of the freshener product rotary dispensing cap.

3. The air freshener for motor vehicles according to claim 2, wherein at a point of a bottom edge of the bushing integral with the inside of the rotary dispensing cap there is a protruding anchoring tab that fixes a position of the bushing during rotary dispensing cap turning movements, and the anchoring tub is only displaced by exerting greater pressure when unscrewing the rotary dispensing cap from the freshener product container to proceed to replace the rotary dispensing cap when the freshener product is used up.

\* \* \* \* \*